*(12)* United States Patent
Lambert et al.

US011460467B2

(10) Patent No.: US 11,460,467 B2
(45) Date of Patent: Oct. 4, 2022

(54) DIAGNOSIS METHOD FOR LUPUS

(71) Applicants: INSERM (Institut National de la Sante et da la Recherche Medicale), Paris (FR); Universite d'Aix Marseille, Marseilles (FR); GFRS (Groupe Francophone de Recherche sur la Sclerodermie Systemique), Paris (FR)

(72) Inventors: Nathalie Lambert, Marseilles (FR); Fanny Arnoux, Marseilles (FR); Doua Azzouz, Marseilles (FR)

(73) Assignees: INSERM (Institut National de la Santé et de la Recherche Médicale), Paris (FR); Université d'Aix Marseille, Marseilles (FR); GFRS (Groupe Francophone de Recherche sur la Sclerodermie Systemique), Paris (FR)

( * ) Notice: Subject to any disclaimer, the term of this patent is extended or adjusted under 35 U.S.C. 154(b) by 374 days.

(21) Appl. No.: 16/269,596

(22) Filed: Feb. 7, 2019

(65) Prior Publication Data

US 2019/0195871 A1    Jun. 27, 2019

Related U.S. Application Data

(63) Continuation of application No. 15/125,409, filed as application No. PCT/EP2015/055233 on Mar. 12, 2015, now abandoned.

(30) Foreign Application Priority Data

Mar. 13, 2014   (EP) .................................. 14305364

(51) Int. Cl.
    *G01N 33/53*    (2006.01)
    *G01N 33/564*   (2006.01)

(52) U.S. Cl.
    CPC ..... *G01N 33/564* (2013.01); *G01N 2800/104* (2013.01)

(58) Field of Classification Search
    CPC .......... G01N 33/564; G01N 2800/104; G01N 2470/00; G01N 2470/04; G01N 2470/06; G01N 2470/10; G01N 2470/12
    See application file for complete search history.

(56) References Cited

U.S. PATENT DOCUMENTS

2008/0254482 A1 * 10/2008 Mattoon ................. A61P 37/06
                                                        435/7.1
2017/0074876 A1 *  3/2017 Lambert .............. G01N 33/564

FOREIGN PATENT DOCUMENTS

WO    WO-2014016284 A1 *  1/2014 ........... G01N 33/564

OTHER PUBLICATIONS

Azzouz et al. (PLOS,2016, pp. 1-16).*
Harlow & Lane (Harlow, E. and Lane, D., Antibodies: A Laboratory Manual (1988) Cold Spring Harbor Laboratory Press, Cold Spring Harbor, NY, pp. 23-26).*
Mosca et al. (Clin Exp Rheumatol 2011; 29 (Suppl. 68):S126-S129).*
Genth et al (2001;Zeitschrift fur Rheumatologie vol. 60 Issue: 6 ages: 464-8 English Abstract).*
Mayeux et al. ("Biomarkers: Potential uses and Limitations"; NeuroRx (2004); vol. 1, pp. 182-188).*

* cited by examiner

*Primary Examiner* — Carmencita M Belei
(74) *Attorney, Agent, or Firm* — WCF IP (57) ABSTRACT

The present invention relates to an in vitro method for diagnosing lupus in a subject, said method comprising the step of detecting in a biological sample obtained from the subject the autoantibody recognizing the protein biomarker THEX1. More, the invention relates to kits and array useful for carrying out diagnosis methods according to the present invention.

1 Claim, 3 Drawing Sheets

Specification includes a Sequence Listing.

DIAGNOSIS METHOD FOR LUPUS

FIELD OF THE INVENTION

The present invention relates to an in vitro method for diagnosing lupus in a subject, said method comprising the step of detecting in a biological sample obtained from the subject the autoantibody recognizing the protein biomarker THEX1.

More, the invention relates to kits and array useful for carrying out diagnosis methods according to the present invention.

BACKGROUND OF THE INVENTION

Systemic lupus erythematosus (SLE) or lupus is a chronic autoimmune disease that can affect the joints and almost every major organ in the body, including heart, kidneys, skin, lungs, blood vessels, liver, and the nervous system. As in other autoimmune diseases, the body's immune system attacks the body's own tissues and organs, leading to inflammation. A person's risk to develop lupus appears to be determined mainly by genetic factors, but environmental factors, such as infection or stress may trigger the onset of the disease. The course of lupus varies, and is often characterised by alternating periods of flares, i.e. increased disease activity, and periods of remission. Subjects with lupus may develop a variety of conditions such as lupus nephritis, musculoskeletal complications, haematological disorders and cardiac inflammation.

It takes on average 4 years to obtain a correct diagnosis for lupus, in part due to the range and complexity of symptoms and the necessity to discount other possible causes. The American College of Rheumatologists has established eleven criteria to assist in the diagnosis of lupus for the inclusion of patients in clinical trials and developed the SLE Disease Activity Index (SLEDAI) to assess lupus activity. In addition to considering medical history, the subject's age and gender and a physical examination, a number of laboratory tests are also available to assist in diagnosis. These include tests for the presence of antinuclear antibodies (ANA) and tests for other auto-antibodies such as anti-DNA, anti-Sm, anti-RNP, anti-Ro (SSA), anti-Lb (SSB) and anti-cardiolipin antibodies. Other diagnostic tools include tests for serum complement levels, urine analysis, and biopsies of an affected organ. Some of these criteria are very specific for lupus but have poor sensitivity, but none of these tests provides a definitive diagnosis and so the results of multiple differing tests must be integrated to enable a clinical judgement by an expert. For example, a positive ANA test can occur due to infections or rheumatic diseases, and even healthy people without lupus can test positive. The ANA test has high sensitivity (93%) but low specificity (57%). Antibodies to double-stranded DNA and/or nucleosomes were associated with lupus over 50 years ago and active lupus is generally associated with IgG. The sensitivity and specificity of the Farr test for anti-DNA is 78.8% and 90.9%, respectively. Thus it is clear that the status of multiple autoantibody species can provide information on the lupus status of a patient. However, in case when classical markers are absent, a new strong marker may help to diagnose Lupus.

Many autoantibody species have been described in connection with lupus and their cognate antigens include numerous classes of proteins, subcellular organs such as the nucleus and non-protein species such as phospholipid and DNA. Frequently the antigen is either poorly described or uncharacterised at the molecular level e.g. antimitochondrial antibodies. Given the challenges in obtaining a correct diagnosis, there is a need for new or improved in vitro tests with better specificity and sensitivity to enable non-invasive diagnosis of lupus.

Lupus occurs approximately 10 times more frequently in women than in men. It is part of a family of closely related disorders known as the connective tissue diseases which also includes rheumatoid arthritis (RA), polymyositis-dermatomyositis (PM-DM), systemic sclerosis (SSc or scleroderma), Sjogren's syndrome (SS) and various forms of vasculitis. These diseases share a number of clinical symptoms and abnormalities. Subjects suffering from lupus can present with a variety of diverse symptoms, many of which occur in other connective tissue diseases, fibromalgia, dermatomyositis or haematological condition such as idiopathic thrombocytopenic purpura. Diagnosis can therefore be challenging.

SSc patients share many auto-antibodies with SLE patients; nevertheless presence of anti-topoisomerase or anti-centromere autoantibodies remains highly discriminating for SSc diagnosis. By opposition, patients with SSc who do not have ATA or ACA are difficult to diagnose or classify.

Inventors first selected candidate proteins specific of SSc recognized by patients without ACA or ATA by screening 9483 proteins from Invitrogen ProtoArrays® with a very stringent approach. Six candidates remained from this first selection and were further validated for specificity by ELISA on a large group of patients including SLE, Rheumatoid Arthritis (RA), Psoriatic Arthritis (PsoA), Ankylosing Spondylitis (AS), and healthy controls.

SUMMARY OF THE INVENTION

After analyses, inventors identified strong correlations between lupus and presence of autoantibodies against Three prime Histone mRNA EXonuclease 1 (THEX1) protein. Furthermore, they defined that lower concentrations of antigen could reveal whether a patient had lupus or not with a specificity of 94% and a sensitivity of 53%. Detection of THEX1 autoantibodies in a plasma/sera sample is a diagnostic marker for SLE, but could also be a prognostic marker as levels of autoantibodies are higher when disease is more severe.

In the current study, the inventors selected the protein THEX1 from ProtoArray® analysis with a very stringent approach and validated their specificity by ELISA on a larger group of patients and controls.

Thus, the present invention relates to an in vitro method for diagnosing lupus in a subject, said method comprising the step of detecting in a biological sample obtained from the subject the autoantibody recognizing the protein biomarker THEX1.

More, the invention relates to kits and array useful for carrying out diagnosis methods according to the present invention.

DETAILED DESCRIPTION OF THE INVENTION

In one aspect, the present invention provides an in vitro method for diagnosing lupus in a subject, said method comprising the step of detecting in a biological sample obtained from the subject the autoantibody recognizing the protein biomarkers THEX1.

The method of the invention may comprise steps of: contacting the biological sample with a the protein biomarker for a time and under conditions allowing protein biomarker-antibody complexes to form between the protein biomarker and the autoantibody present in the biological sample; and detecting any protein biomarker-antibody complex formed.

In the methods of diagnosis provided herein, the step of detecting any protein biomarker-antibody complex formed between a protein biomarker and an autoantibody present in the biological sample may be performed by any suitable method. In certain embodiments, the detection is by immunoassay.

In particular embodiments, the protein biomarker or biomarkers used in the diagnosis method is/are immobilized on a solid carrier or support.

Typically, the methods of diagnosis may further comprise measuring, in a biological sample obtained from the subject, the concentration of at least one lupus biomarker also known for lupus diagnosis (see for example Sherer Y et al., 2004), for detecting the presence of lupus-specific autoantibodies, such as anti-nuclear antibody (ANA) or anti-extractable nuclear antigen (ENA).

In another aspect, the present invention provides kits for the in vitro diagnosis of lupus in a subject. These kits comprise: the protein biomarker of the invention and at least one reagent for detecting a protein biomarker-antibody complex formed between the protein biomarker and an autoantibody present in the biological sample to be tested. In the kits, the protein biomarker may be immobilized on a solid carrier or support, or alternatively, reagents may be included in the kit that can be used to immobilize the protein biomarker on a solid carrier or support. The kits may further comprise instructions for carrying out a method of diagnosis according to the present invention. In certain embodiments, the kit comprises at the protein biomarker THEX1 or fragments thereof.

In certain embodiments, these kits further comprise at least one additional lupus biomarker also known for the lupus diagnosis, for detecting the presence of lupus-specific autoantibodies as described in Sherer Y et al., 2004. For example, the additional lupus biomarker also known for lupus diagnosis include, but are not limited to nuclear antigen or extractable nuclear antigen.

In particular embodiments, these kits further comprise at least one additional lupus biomarker also known for lupus diagnosis as described below for detecting the presence of lupus-specific autoantibodies, such as anti-nuclear antibody (ANA) or anti-extractable nuclear antigen (ENA).

In yet another aspect, the present invention provides arrays for the diagnosis of lupus in a subject. An array according to the invention comprises, attached to its surface, the protein biomarker of the invention. The array comprises, attached to its surface, the protein bio marker including THEX1 described herein.

In certain preferred embodiments, an inventive array further comprises at least one additional lupus biomarker also known for the lupus diagnosis, for detecting the presence of lupus-specific autoantibodies as described in Sherer Y et al., 2004. For example, the additional lupus biomarker also known for lupus diagnosis include, but are not limited to nuclear antigen or extractable nuclear antigen.

In particular embodiments, the array further comprises, attached to its surface, at least one additional lupus biomarker also known for lupus diagnosis as described below for detecting the presence of lupus-specific autoantibodies, such as anti-nuclear antibody (ANA) or anti-extractable nuclear antigen (ENA).

These and other objects, advantages and features of the present invention will become apparent to those of ordinary skill in the art having read the following detailed description of the preferred embodiments.

Definitions

Throughout the specification, several terms are employed that are defined in the following paragraphs.

As used herein, the term "subject" refers to a human or another mammal (e.g., primate, dog, cat, goat, horse, pig, mouse, rat, rabbit, and the like), that can be afflicted with lupus. In a particular embodiment of the present invention, the subject is a human being. In such embodiments, the subject is often referred to as an "individual". The term "individual" does not denote a particular age, and thus encompasses children, teenagers, and adults.

The term "subject suspected of having lupus" refers to a subject that presents one or more symptoms indicative of lupus (e.g., fever, malaise, joint pains, myalgias, fatigue), or that is screened for lupus (e.g., during a physical examination). Alternatively or additionally, a subject suspected of having lupus may have one or more risk factors (e.g., age, sex, family history, smoking, etc). The term encompasses subjects that have not been tested for lupus as well as subjects that have received an initial diagnosis.

The term "biological sample" is used herein in its broadest sense. A biological sample is generally obtained from a subject. A sample may be of any biological tissue or fluid with which biomarker of the present invention may be assayed. Frequently, a sample will be a "clinical sample", i.e., a sample derived from a patient. Such samples include, but are not limited to, bodily fluids which may or may not contain cells, e.g., blood (e.g., whole blood, serum or plasma), synovial fluid, saliva, tissue or fine needle biopsy samples, and archival samples with known diagnosis, treatment and/or outcome history. Biological samples may also include sections of tissues such as frozen sections taken for histological purposes. The term "biological sample" also encompasses any material derived by processing a biological sample. Derived materials include, but are not limited to, cells (or their progeny) isolated from the sample, or proteins extracted from the sample. Processing of a biological sample may involve one or more of: filtration, distillation, extraction, concentration, inactivation of interfering components, addition of reagents, and the like.

In a particular embodiment of the invention, the biological sample is a serologic sample or is derived from whole blood, serum or plasma obtained from a subject.

The terms "normal" and "healthy" are used herein interchangeably. They refer to a subject that has not presented any lupus symptoms, and that has not been diagnosed with lupus. Particularly, a normal subject is not on medication for lupus and has not been diagnosed with any other autoimmune disease and had no family history of autoimmunity. In certain embodiments, normal subjects may have similar sex, age, and/or body mass index as compared with the subject from which the biological sample to be tested was obtained. The term "normal" is also used herein to qualify a sample obtained from a healthy subject.

In the context of the present invention, the term "control", when used to characterize a subject, refers to a subject that is healthy or to a patient who has been diagnosed with a specific autoimmune disease other than lupus. The term "control sample" refers to one, or more than one, sample that has been obtained from a healthy subject or from a patient diagnosed with an autoimmune disease other than lupus.

The term "autoantibody", as used herein, has meaning accepted in the art, and refers to an antibody that is produced by the immune system of a subject and that is directed against subject's own proteins. Autoantibodies may attack the body's own cells, tissues, and/or organs, causing inflammation and damage.

As used herein, the term "autoantigen" refers to an endogenous antigen, or an active fragment thereof, that stimulates the production of autoantibodies in a body of a subject, as in autoimmune reactions. The term also encompasses any substances that can form an antigen-antibody complex with autoantibodies present in a subject or in a biological sample obtained from a subject.

The terms "biomarker", "protein biomarker" and "marker" are used herein interchangeably. They refer to a substance that is a distinctive indicator of a biological process, biological event, and/or pathologic condition. In the context of the present invention, the term "biomarker of lupus" or "lupus biomarker" encompasses THEX1 protein provided herein which are specifically recognized by anti-THEX1 autoantibodies present in a biological sample (e.g., blood sample) of a lupus patient. In certain preferred embodiments, the biomarkers of the invention are proteins fragment of less than 20 amino acids. In more preferred embodiments, the biomarkers of the invention are proteins fragment of between 5 and 20 amino acids (i.e. 10 or 15 amino acids).

As used herein, the term "indicative of lupus", when applied to a process or event, refers to a process or event which is a diagnostic of lupus, such that the process or event is found significantly more often in subjects with lupus than in healthy subjects and/or in subjects suffering from a disease other than lupus.

The terms "protein", "polypeptide", and "peptide" are used herein interchangeably, and refer to amino acid sequences of a variety of lengths, either in their neutral (uncharged) forms or as salts, and either unmodified or modified by glycosylation, side chain oxidation, or phosphorylation, or citrullination. In certain embodiments, the amino acid sequence is a full-length native protein. In other embodiments, the amino acid sequence is a smaller fragment of the full-length protein. In still other embodiments, the amino acid sequence is modified by additional substituents attached to the amino acid side chains, such as glycosyl units, lipids, or inorganic ions such as phosphates, as well as modifications relating to chemical conversion of the chains such as oxidation of sulfhydryl groups. Thus, the term "protein" (or its equivalent terms) is intended to include the amino acid sequence of the full-length native protein, or a fragment thereof, subject to those modifications that do not significantly change its specific properties. In particular, the term "protein" encompasses protein isoforms, i.e., variants that are encoded by the same gene, but that differ in their pI or MW, or both. Such isoforms can differ in their amino acid sequence (e.g., as a result of alternative splicing or limited proteolysis), or in the alternative, may arise from differential post-translational modification (e.g., glycosylation, acylation, phosphorylation).

The term "analog", when used herein in reference to a protein or polypeptide, refers to a peptide that possesses a similar or identical function as the protein or polypeptide but need not necessarily comprise an amino acid sequence that is similar or identical to the amino acid sequence of the protein or polypeptide or a structure that is similar or identical to that of the protein or polypeptide. Preferably, in the context of the present invention, an analog has an amino acid sequence that is at least 80%, more preferably, at least about: 80%, 85%, 90%, 95%, 96%, 97%, 98% or 99%, identical to the amino acid sequence of the protein or polypeptide. In certain preferred embodiments, an analog of a peptide biomarker of the invention has an amino acid sequence that is at least 80% identical or at least 85% identical to the amino acid sequence of the peptide biomarker.

The term "homologous" (or "homology"), as used herein, is synonymous with the term "identity" and refers to the sequence similarity between two polypeptide molecules or between two nucleic acid molecule. When a position in both compared sequences is occupied by the same base or same amino acid residue, then the respective molecules are homologous at that position. The percentage of homology between two sequences corresponds to the number of matching or homologous positions shared by the two sequences divided by the number of positions compared and multiplied by 100. Generally, a comparison is made when two sequences are aligned to give maximum homology. Homologous amino acid sequences share identical or similar amino acid sequences. Similar residues are conservative substitutions for, or "allowed point mutations" of, corresponding amino acid residues in a reference sequence. "Conservative substitutions" of a residue in a reference sequence are substitutions that are physically or functionally similar to the corresponding reference residue, e.g., that have a similar size, shape, electric charge, chemical properties, including the ability to form covalent or hydrogen bonds, or the like. Particularly preferred conservative substitutions are those fulfilling the criteria defined for an "accepted point mutation" by Dayhoff et al. ("Atlas of Protein Sequence and Structure", 1978, Nat. Biomed. Res. Foundation, Washington, D.C., Suppl. 3, 22: 354-352).

The terms "labeled", "labeled with a detectable agent" and "labeled with a detectable moiety" are used herein interchangeably. These terms are used to specify that an entity (e.g., a THEX1 protein) can be visualized, for example, following binding to another entity (e.g., an anti-THEX1 autoantibodies). Preferably, a detectable agent or moiety is selected such that it generates a signal which can be measured and whose intensity is related to the amount of bound entity. In array-based methods, a detectable agent or moiety is also preferably selected such that it generates a localized signal, thereby allowing spatial resolution of the signal from each spot on the array. Methods for labeling proteins and polypeptides are well-known in the art. Labeled polypeptides can be prepared by incorporation of or conjugation to a label, that is directly or indirectly detectable by spectroscopic, photochemical, biochemical, immunochemical, electrical, optical, or chemical means, or any other suitable means. Suitable detectable agents include, but are not limited to, various ligands, radionuclides, fluorescent dyes, chemiluminescent agents, microparticles, enzymes, colorimetric labels, magnetic labels, and haptens.

The terms "protein array" and "protein chip" are used herein interchangeably. They refer to a substrate surface on which different proteins or polypeptides are immobilized, in an ordered manner, at discrete spots on the substrate. Protein arrays may be used to identify protein/protein interactions (e.g., antigen/antibody interactions), to identify the substrates of enzymes, or to identify the targets of biologically active small molecules. The term "microarray" specifically refers to an array that is miniaturized so as to require microscopic examination for visual evaluation.

The term "THEX1", refers to the protein named "three prime histone mRNA exonuclease 1". The sequence of said protein may be found under the NCBI Reference:

NM_153332.2. Protein THEX1 identified as described herein has the following amino acid sequence:

```
SEQ ID No 1:
MEDPQSKEPAGEAVALALLESPRPEGGEEPPRPSPEETQQCKEDGQETKG

SKFITSSASDFSDPVYKEIAITNGCINRMSKEELRAKLSEFKLETRGVKD

VLKKRLKNYYKKQKLMLKESNFADSYYDYICIIDFEATCEEGNPPEFVHE

IIEFPVVLLNTHTLEIEDTFQQYVRPEINTQLSDFCISLTGITQDQVDRA

DTFPQVLKKVIDWMKLKELGTKYKYSLLTDGSWDMSKFLNIQCQLSRLKY

PPFAKKWINIRKSYGNEYKVPRSQTKLTIMLEKLGMDYDGRPHCGLDDSK

NIARIAVRMLQDGCELRINEKMHAGQLMSVSSSLPIEGTPPPQMPHFRK.
```

To be understood broadly, the term "THEX1" refers to the protein and also to analogs and fragments of the protein. The term "THEX1 fragment", refers to a peptide comprising an amino acid sequence of at least 5 amino acid residues (preferably, of at least: 10, 15, 20, 25, 30, 40, 50, 60, or 70 amino acid residues) of the amino acid sequence of a THEX1 protein. In preferred embodiments of the present invention, a fragment of THEX1 biomarker of the invention comprises an amino acid sequence of at least 5 consecutive amino acid residues of the amino acid sequence of the peptide bio marker and is not the whole protein.

Detailed Description of Certain Preferred Embodiments

As mentioned above, the present invention provides a biomarker that can be used for detecting the presence of lupus-specific autoantibodies in biological samples obtained from patients. This biomarker is THEX1 protein which respectively and specifically reacts with anti-THEX1 autoantibodies, present in the serum or plasma of lupus patients.

Other lupus biomarker also known for the lupus diagnosis as described in Sherer Y et al., 2004 may be used in the diagnostic methods of the present invention. For example, the additional lupus biomarker also known for the lupus diagnosis may be selected in the group consisting of nuclear antigen or extractable nuclear antigen.

The invention also provides methods for using these biomarkers in the diagnosis of lupus.

The invention also provides a biomarker that can be used for diagnosing the severity of lupus in lupus patients by detecting the presence of lupus-specific autoantibodies in biological samples obtained from patients. This biomarker is THEX1 protein which respectively and specifically reacts with anti-THEX1 autoantibodies, present in the serum or plasma of lupus patients.

As demonstrated by the inventors, the level of anti-THEX1 autoantibodies is correlated with the severity of the disease.

The invention also provides methods for using the biomarker THEX1 in methods for diagnosing the severity of lupus.

I—Protein Biomarkers
Preparation of the Protein Biomarkers

The polypeptide/protein biomarkers of the present invention may be prepared by any suitable method, including recombinant methods. Such methods, as described, for example, in "The Proteins" (Vol. II, 3rd Ed., H. Neurath et al. (Eds.), 1976, Academic Press: New York, N.Y., pp. 105-237) may also be used to synthesize the biomarkers of the invention.

In certain embodiments, a polypeptide/protein biomarker of the invention is provided which is immobilized onto a solid carrier or support (e.g., a bead or array). Methods for immobilizing polypeptide molecules onto a solid surface are known in the art. A polypeptide/protein may be immobilized by being either covalently or passively bound to the surface of a solid carrier or support. Examples of suitable carrier or support materials include, but are not limited to, agarose, cellulose, nitrocellulose, dextran, Sephadex, Sepharose, carboxymethyl cellulose, polyacrylamides, polystyrene, polyvinyl chloride, polypropylene, filter paper, magnetite, ion-exchange resin, glass, polyamine-methyl-vinyl-ether-maleic acid copolymer, amino acid copolymer, ethylene-maleic acid copolymer, nylon, silk, and the like. Immobilization of a polypeptide/protein biomarker on the surface of a solid carrier or support may involve crosslinking, covalent binding or physical adsorption, using methods well known in the art. The solid carrier or support may be in the form of a bead, a particle, a microplate well, an array, a cuvette, a tube, a membrane, or any other shape suitable for conducting a diagnostic method according to the invention (e.g., using an immunoassay).

In particular, the invention provides an array or protein array for the diagnosis of lupus, comprising, immobilized to its surface, the protein biomarker of the invention.

In a particular, the quantity of the protein biomarker used for the array may be but is not limited to 0.2 µg/well, 0.1 µg/well, 0.05 µg/well.

The array may further comprises at least one additional lupus biomarker also known for the lupus, diagnosis for detecting the presence of lupus-specific autoantibodies as described in Sherer Y et al., 2004. For example, the additional lupus biomarker also known for the lupus diagnosis may be selected in the group consisting of nuclear antigen or extractable nuclear antigen.

The present invention also provides a protein bead suspension array for the diagnosis of lupus. This bead suspension array comprises a suspension of one or more identifiable distinct particles or beads, wherein each bead contains coding features relating to its size, color or fluorescence signature and wherein each bead is coated with a polypeptide/protein biomarker of the present invention. Examples of bead suspension arrays include thexMAP® bead suspension array (Luminex Corporation).

II—Methods of Diagnosis

The present invention provides methods for the diagnosis of lupus in a subject. Such methods comprise contacting a biological sample obtained from the subject to be tested with the biomarker of the invention for a time and under conditions allowing a biomarker-antibody complex to form; and detecting the biomarker-antibody complexes formed.

The biomarker of the invention is THEX1.

In this method, the detection of a biomarker-antibody complex is indicative of lupus in the subject.

In another embodiment, the biological sample obtained from the subject is in contact with other protein biomarkers selected from the group consisting of nuclear antigen or extractable nuclear antigen.

In a particular embodiment, the subject of the invention has no autoantibodies recognizing one or more protein biomarkers selected from the group of proteins consisting of nuclear antigen or extractable nuclear antigen.

In one embodiment, the invention relates to a method for diagnosing lupus in a subject, said method comprising the step of detecting anti-THEX1 autoantibodies complexes.

In another aspect, the invention provides an in vitro method for diagnosing the severity of lupus in a subject, said method comprising the step of detecting in a biological sample obtained from the subject the autoantibody recognizing the protein biomarkers THEX1.

Biological Samples

The method of diagnosis of the present invention may be applied to any type of biological sample allowing one or more biomarkers to be assayed. Examples of suitable biological samples include, but are not limited to, whole blood, serum, plasma, saliva, and. Biological samples used in the practice of the invention may be fresh or frozen samples collected from a subject, or archival samples with known diagnosis, treatment and/or outcome history. Biological samples may be collected by any non-invasive means, such as, for example, by drawing blood from a subject, or using fine needle aspiration or needle biopsy. In certain embodiments, the biological sample is a serologic sample and is selected from the group consisting of whole blood, serum, plasma.

In preferred embodiments, the inventive methods are performed on the biological sample itself without, or with limited, processing of the sample.

However, alternatively, the inventive methods may be performed on a protein extract prepared from the biological sample. In this case, the protein extract preferably contains the total protein content. Methods of protein extraction are well known in the art (see, for example "Protein Methods", D. M. Bollag et al., 2nd Ed., 1996, Wiley-Liss; "Protein Purification Methods: A Practical Approach", E. L. Harris and S. Angal (Eds.), 1989; "Protein Purification Techniques: A Practical Approach", S. Roe, 2nd Ed., 2001, Oxford University Press; "Principles and Reactions of Protein Extraction, Purification, and Characterization", H. Ahmed, 2005, CRC Press: Boca Raton, Fla.). Various kits can be used to extract proteins from bodily fluids and tissues. Such kits are commercially available from, for example, BioRad Laboratories (Hercules, Calif.), BD Biosciences Clontech (Mountain View, Calif.), Chemicon International, Inc. (Temecula, Calif.), Calbiochem (San Diego, Calif.), Pierce Biotechnology (Rockford, Ill.), and Invitrogen Corp. (Carlsbad, Calif.). User Guides that describe in great detail the protocol to be followed are usually included in all these kits. Sensitivity, processing time and costs may be different from one kit to another. One of ordinary skill in the art can easily select the kit(s) most appropriate for a particular situation.

Detection of Biomarker-Antibody Complexes

The diagnostic methods of the present invention involve detection of a biomarker-antigen complex formed between the protein biomarker and an autoantibody present in the biological sample tested. In the practice of the invention, detection of such a complex may be performed by any suitable method (see, for example, E. Harlow and A. Lane, "Antibodies: A Laboratories Manual", 1988, Cold Spring Harbor Laboratory: Cold Spring Harbor, N.Y.).

For example, detection of a biomarker-antibody complex may be performed using an immunoassay. A wide range of immunoassay techniques is available, including radioimmunoassay, enzyme immunoassays (EIA), enzyme-linked immunosorbent assays (ELISA), and immunofluorescence immunoprecipitation. Immunoassays are well known in the art. Methods for carrying out such assays as well as practical applications and procedures are summarized in textbooks. Examples of such textbooks include P. Tijssen, In: Practice and theory of enzyme immunoassays, eds. R. H. Burdon and v. P. H. Knippenberg, Elsevier, Amsterdam (1990), pp. 221-278 and various volumes of Methods in Enzymology, Eds. S. P. Colowick et al., Academic Press, dealing with immunological detection methods, especially volumes 70, 73, 74, 84, 92 and 121. Immunoassays may be competitive or non-competitive.

For example, any of a number of variations of the sandwich assay technique may be used to perform an immunoassay. Briefly, in a typical sandwich assay applied to the detection of, for example, anti-THEX1 autoantibodies according to the present invention, an unlabeled THEX1-protein/polypeptide biomarker is immobilized on a solid surface (as described above) and the biological sample to be tested is brought into contact with the bound biomarker for a time and under conditions allowing formation of a biomarker-antibody complex. Following incubation, an antibody that is labelled with a detectable moiety and that specifically recognizes antibodies from the species tested (e.g., an anti-human IgG for human subjects) is added and incubated under conditions allowing the formation of a ternary complex between any biomarker-bound autoantibody and the labelled antibody. Any unbound material is washed away, and the presence of any anti-THEX1 autoantibody in the sample is determined by observation/detection of the signal directly or indirectly produced by the detectable moiety. Variations on this assay include an assay, in which both the biological sample and the labeled antibody are added simultaneously to the immobilized THEX1-protein/polypeptide biomarker.

The second antibody (i.e., the antibody added in a sandwich assay as described above) may be labeled with any detectable moiety, i.e., any entity which, by its chemical nature, provides an analytically identifiable signal allowing detection of the ternary complex, and consequently detection of the biomarker-antibody complex.

Detection may be either qualitative or quantitative. Methods for labelling biological molecules such as antibodies are well-known in the art (see, for example, "Affinity Techniques. Enzyme Purification: Part B", Methods in Enzymol., 1974, Vol. 34, W. B. Jakoby and M. Wilneck (Eds.), Academic Press: New York, N.Y.; and M. Wilchek and E. A. Bayer, Anal. Biochem., 1988, 171: 1-32).

The most commonly used detectable moieties in immunoassays are enzymes and fluorophores. In the case of an enzyme immunoassay (EIA or ELISA), an enzyme such as horseradish perodixase, glucose oxidase, beta-galactosidase, alkaline phosphatase, and the like, is conjugated to the second antibody, generally by means of glutaraldehyde or periodate. The substrates to be used with the specific enzymes are generally chosen for the production of a detectable color change, upon hydrolysis of the corresponding enzyme. In the case of immunofluorescence, the second antibody is chemically coupled to a fluorescent moiety without alteration of its binding capacity. After binding of the fluorescently labeled antibody to the biomarker-antibody complex and removal of any unbound material, the fluorescent signal generated by the fluorescent moiety is detected, and optionally quantified. Alternatively, the second antibody may be labeled with a radioisotope, a chemiluminescent moiety, or a bioluminescent moiety.

Lupus Diagnosis

In the method of the present invention, detection of a biomarker-antibody complex is indicative of the presence of THEX1 autoantibodies in the biological sample tested and is therefore indicative of lupus in the subject from which the biological sample is obtained. Thus, the methods of the present invention may be used for the diagnosis of lupus in patients. In particular, the method of the invention may be used for testing subjects suspected of having lupus or may be used for testing the severity of the lupus in subjects.

It will be appreciated by one skilled in the art that diagnosis of lupus may be performed solely on the basis of the results obtained by a method provided herein. Alternatively, a physician may also consider other clinical or pathological parameters used in existing methods to diagnose lupus. Thus, results obtained using methods of the present invention may be compared to and/or combined with results from other tests, assays or procedures performed for the diagnosis of lupus. Such comparison and/or combination may help provide a more refine diagnosis.

For example, lupus diagnosis methods of the present invention may be used in combination with lupus criteria [Tan E M et al., 1982; Hochberg M C, 1997; Petri M et al., 2012].

Alternatively or additionally, results from lupus diagnosis methods of the present invention may be used in combination with results from one or more assays that employ other lupus biomarkers. Thus, in certain embodiments, diagnosis of lupus may be based on results from a method of the invention and on results from one or more additional assays that use a different lupus biomarker. For example, a panel of lupus biomarkers may be tested either individually or simultaneously, e.g., using a chip or a bead-based array technology.

Examples of suitable lupus biomarkers include lupus biomarker also known for the lupus diagnosis as described in Sherer Y et al., 2004. For example, suitable lupus biomarker also known for the diagnostic of lupus include, but are not limited to nuclear antigen or extractable nuclear antigen.

In another embodiment, the method according to the invention the biological sample obtained from the subject is in contact with the biomarker of the invention and one or more protein bio markers selected from the group of proteins consisting of a lupus bio marker also known for the diagnostic of lupus as described in Sherer Y et al., 2004. For example, suitable lupus biomarker also known for the diagnostic of lupus include, but are not limited to nuclear antigen or extractable nuclear antigen.

III—Kits

In another aspect, the present invention provides kits comprising materials useful for carrying out a diagnostic method according to the present invention. The diagnosis procedures provided herein may be performed by diagnostic laboratories, experimental laboratories, or practitioners. The invention provides kits that can be used in these different settings.

Materials and reagents for detecting anti-THEX1 autoantibodies in a biological sample and/or for diagnosing lupus, in a subject according to the present invention may be assembled together in a kit. Each kit of the invention comprises at least one protein/polypeptide biomarker of the invention preferably in an amount that is suitable for detection of autoantibodies in a biological sample.

Thus, in certain embodiments, a kit of the invention comprises THEX1 biomarker.

In another embodiment, the present invention provides kits comprising materials useful for diagnosing the severity of lupus in a subject.

The peptide biomarker(s) included in a kit may or may not be immobilized on the substrate surface (e.g., beads, array, and the like). Thus, in preferred embodiments, the kit of the invention includes an array for diagnosing lupus as provided herein. Alternatively, a substrate surface may be included in a kit of the invention for immobilization of the peptide biomarkers.

A kit of the invention generally also comprises at least one reagent for the detection of a biomarker-antibody complex formed between the peptide biomarker included in the kit and an autoantibody present in a biological sample. Such a reagent may be, for example, a labelled antibody that specifically recognizes antibodies from the species tested (e.g., an anti-human IgG for human subjects), as described above.

Depending on the procedure, the kit may further comprise one or more of the following: extraction buffer and/or reagents, blocking buffer and/or reagents, immuno-detection buffer and/or reagents, labelling buffer and/or reagents, and detection means. Protocols for using these buffers and reagents for performing different steps of the procedure may be included in the kit.

The different reagents included in the kit of the invention may be supplied in a solid (e.g., lyophilized) or liquid form. The kits of the present invention may optionally comprise different containers (e.g., vial, ampoule, test tube, flask or bottle) for each individual buffer and/or reagent. Each component will generally be suitable as aliquoted in its respective container or provided in a concentrated form. Other containers suitable for conducting certain steps of the disclosed methods may also be provided. The individual containers of the kit are preferably maintained in close confinement for commercial sale.

In certain embodiments, a kit comprises instructions for using its components for the diagnosis of lupus, in a subject according to a method of the invention. Instructions for using the kit according to methods of the invention may comprise instructions for processing the biological sample obtained from the subject and/or for performing the test, and/or instructions for interpreting the results. A kit may also contain a notice in the form prescribed by a governmental agency regulating the manufacture, use or sale of pharmaceuticals or biological products.

The invention will be further illustrated by the following figures and examples. However, these examples and figures should not be interpreted in any way as limiting the scope of the present invention.

FIGURES

SSc: systemic sclerosis; HC: healthy controls; Rheum D: Rheumatic diseases including Rheumatoid Arthritis (RA), Psoriatic Arthritis (PsoA), Ankylosing Spondylitis (AS), SLE: Systemic Lupus Erythematosus P1: p value when compared with HC ($\chi^2$ test, with Bonferroni correction).

P2: p value when compared with Rheum D ($\chi^2$ test with Bonferroni correction).

ns: non significative; NA: non applicable p values<0.05; *p values<0.005; **p values<0.0001 with Mann Whitney test.

SSc: systemic sclerosis; HC: healthy controls; Rheum D: Rheumatic diseases including Rheumatoid Arthritis (RA), Psoriatic Arthritis (PsoA), Ankylosing Spondylitis (AS), SLE: Systemic Lupus Erythematosus P1: p value when compared with HC ($\chi^2$ test, with Bonferroni correction).

P2: p value when compared with Rheum D ($\chi^2$ test with Bonferroni correction).

ns: non significative; NA: non applicable

\*\*\* p values<0.0001 with Mann Whitney test.

P (two-tailed)<0.0001

EXAMPLE

Material & Methods

Participants' Characteristics

For ProtoArray analysis, plasma samples from 20 patients with SSc including 8 patients negative for ATA and ACA (Abneg), 6 positive for ATA and 6 positive for ACA were recruited from 5 French hospitals. Patients with SSc were compared to 18 controls, including 8 healthy individuals with no history of autoimmune diseases (AID) recruited at the Centre d'Examen de Santé de l'Assurance Maladie (CESAM), Marseille, France and 10 patients with other AID including Rheumatoid Arthritis (RA), Systemic Erythematous Lupus (SLE) and Localized Scleroderma (LocSc) recruited in the Rheumatology Unit of St Marguerite Hospital in Marseille. The patients' autoantibody profile (ATA, ACA, Abneg) and patients' disease subtype (Lc-SSc, Dc-SSc) was obtained by reviewing medical records. It is to note that Abneg patients are negative for ATA and ACA but could be positive for other autoantibodies (anti-RNA polymerase III, anti-U3RNP . . . ) but this was not reported in medical records.

After determination of specific proteins by ProtoArrays, ELISA analyses of the six candidate proteins were realized on a larger cohort of patients and controls recruited from the same hospitals and Centers as described above. A total number of maximum 126 patients with SSc, 105 patients with SLE, from whom 84 Disease Activity Index (SLEDAI) was available, 106 patients with RA, all positive for Anti-Citrullinated Protein Antibodies (ACPA), 39 patients with AS, 40 patients with PsoA and 133 healthy controls were tested (data not shown).

Ethics Statements

All participants signed informed consent according to the Declaration of Helsinki [Vollmann J et al., 1996]. The study is registered at the INSERM under the Biomedical Research Protocol number RBM-04-10 or as a collection registered under the number DC-2008-327.

Detection of Autoantibodies by Protein Arrays

ProtoArray human protein microarrays V5.0 (Invitrogen, Carlsbad, Calif., USA) are spotted in duplicate on a nitrocellulose-coated glass slide with 9483 human proteins expressed using a baculovirus expression system, purified from insect cells (protein content list 5.0). Arrays were first blocked to avoid non-specific hybridization with Blocking Buffer (1% BSA, 1× PBS, 0.1% Tween® 20) at 4° C. for 1 hour (PartnerChip, Evry, France). Plasma samples, diluted 1:500 in Probe Buffer (1× PBS, 5 mM MgCl2, 0.5 mM DTT, 5% glycerol, 0.05% Triton® X-100, 1% BSA) were added to arrays and incubated for 90 minutes at 4° C. in an incubation/hybridization chamber. Arrays were then washed 3 times for 8 minutes with 20 ml Probe Buffer, before adding a 1.0 µg/ml solution of anti-human IgG conjugated to Alexa Fluor® 647 (Invitrogen, Carlsbad, Calif., USA) for 90 minutes at 4° C. Arrays were washed again 3 times as described above and dried at room temperature. Arrays were scanned with a NimbleGen MS 200 scanner (Roche, Basel, Switzerland). Fluorescence data acquired with GenePix Pro Software and processed using Protoarray Prospector 5.2 (Invitrogen, Carlsbad, Calif., USA).

ProtoArray® Data Analysis

The ProtoArray® Prospector software includes a linear normalization algorithm that facilitates inter-assay data analysis and M-statistics algorithms for cross-group comparisons important for biomarker identification. These statistical tools allow comparing results between pairs of groups to identify probes which have consistently increased signals in the group of patients with SSc with respect to the control group (healthy individuals and patients with other AID).

Detection of Autoantibodies by ELISA

ProtoArrays allowed to identify six candidates: Fibroblast Growth Factor 2 (FGF2), Allograft Inflammatory Factor 1 (AIF1) transcript variant 1, Ephrin Type B-receptor 2 (EphB2), Dual specificity protein kinase CLK1, Three prime Histone mRNA EXonuclease 1 (THEX1), Ankyrin repeat and Sterile alpha motif domain containing 6 (ANKS6). Candidate proteins were purchased from Invitrogen, except FGF2 which was purchased from Millipore (CA, USA). Plates (Nunc, Kamstrupvej, Denmark) were coated overnight at 4° C. with 0.2 µg of candidate protein per well diluted in PBS (except ANKS6 for which working conditions were defined at 0.1 µg/well and THEX1 which was tested with both concentrations). Plates were blocked with PBS 2% BSA overnight. After blocking solution removal, plasma samples diluted to 1:100 were added. After 2 hours of incubation at room temperature, plates were washed 3 times (1 minute) with PBS 0.1% Tween 20 and peroxidase-conjugated anti-human IgG (Sigma Aldrich, St Quentin-Fallavier, France) was added for half an hour. After washing, plates were then revealed with tetramethylbenzidine (TMB) liquid substrate system (Sigma-Aldrich, St Louis, Mo., USA). Optical density (OD) was read at 405 nm on a PowerWave XS microplate spectrophotometer (Biotek, Colmar, France). For each individual, background OD was obtained by adding plasma on duplicated wells without tested protein. Positive plasma were defined by an OD value superior or equal to twice the background OD (positive ΔOD=0 or more).

Statistical Analysis

To determine whether a candidate protein was significantly better recognized by plasmas from patients with SSc than healthy controls andlor patients with other rheumatic diseases, p values were calculated using the $\chi^2$ test and corrected for multiple comparisons (Bonferroni) As 4 groups were compared (SSc, SLE, HC and other rheumatic diseases including RA, AS and PsoA) a correction by 4 was applied. For ΔOD comparisons between groups, p values were evaluated using Mann Whithney test (Graphpad Prism 5). Correlation between ΔOD and severity of the disease (SLEDAI) for SLE was realized by Spearman's rank correlation.

Results:

THEX1 Titration for a Differential Diagnosis Between SLE and Abneg SSc Patients

We analyzed THEX1 and tested whether 2 different protein concentrations (0.2 and 0.1 µg/well) would discriminate diseases and subgroups of patients with SSc stratified by autoantibody profiles (ATA, ACA, Abneg).

Figure 1:
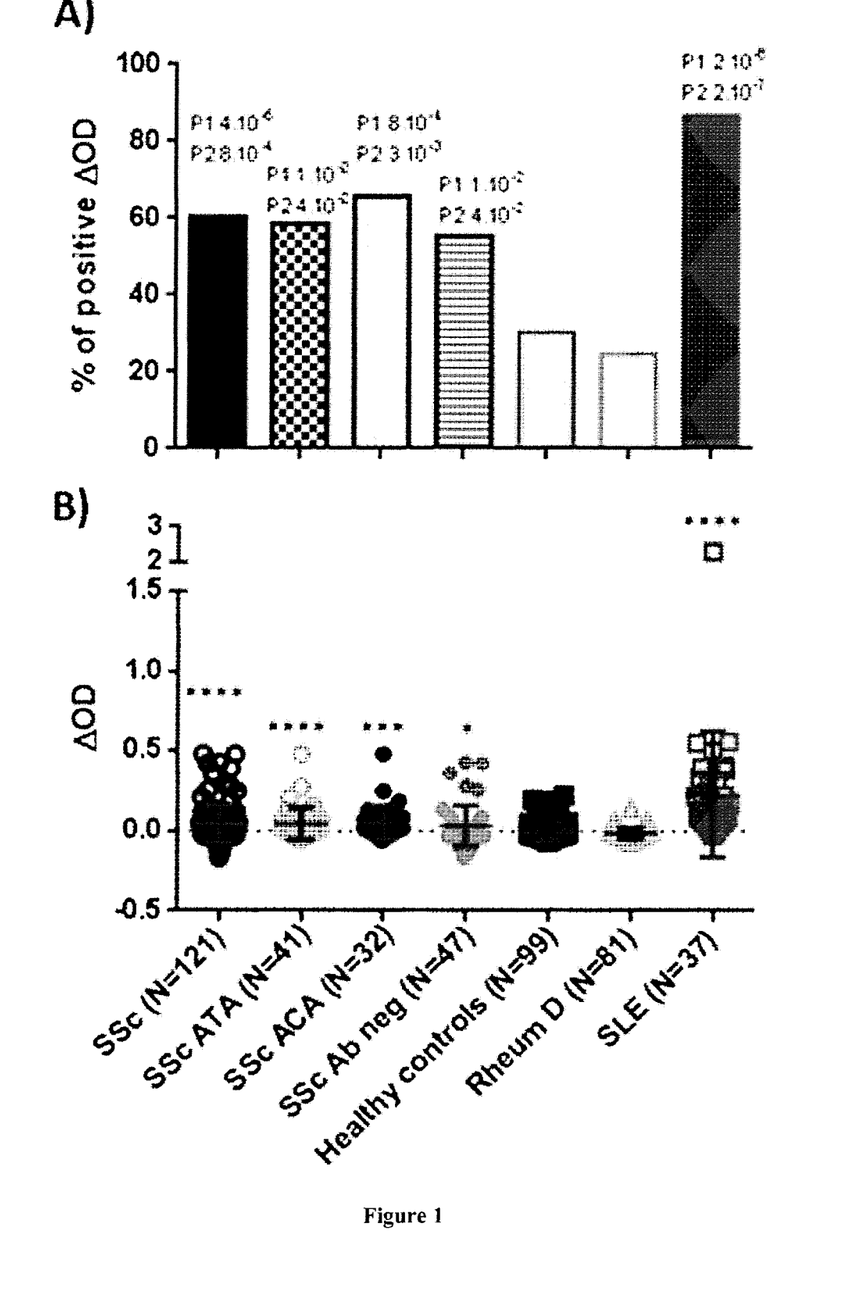
FIG. 1: Autoantibodies to THEX1 (0.2 µg/well) analyzed in subgroups of patients with SSc and other diseases. A) Percentage of positive individuals, B) ΔOD values.

When tested at 0.2 µg/well, THEX1 was only specific of SSc and SLE. It was recognized by all 3 categories of patients with SSc (ATA, ACA and Abneg). Interestingly 55% of Abneg patients (FIG. 1A) significantly recognized this protein with a mean ΔOD of 0.032 (FIG. 1B) versus only 30% of healthy controls (mean ΔOD=−0.001) and 25% of other rheumatic diseases (mean ΔOD=−0.012).

However the highest positivity (87% FIG. 1A) and the highest mean ΔOD (0.231, FIG. 1B) were observed in patients with SLE.

Figure 2:
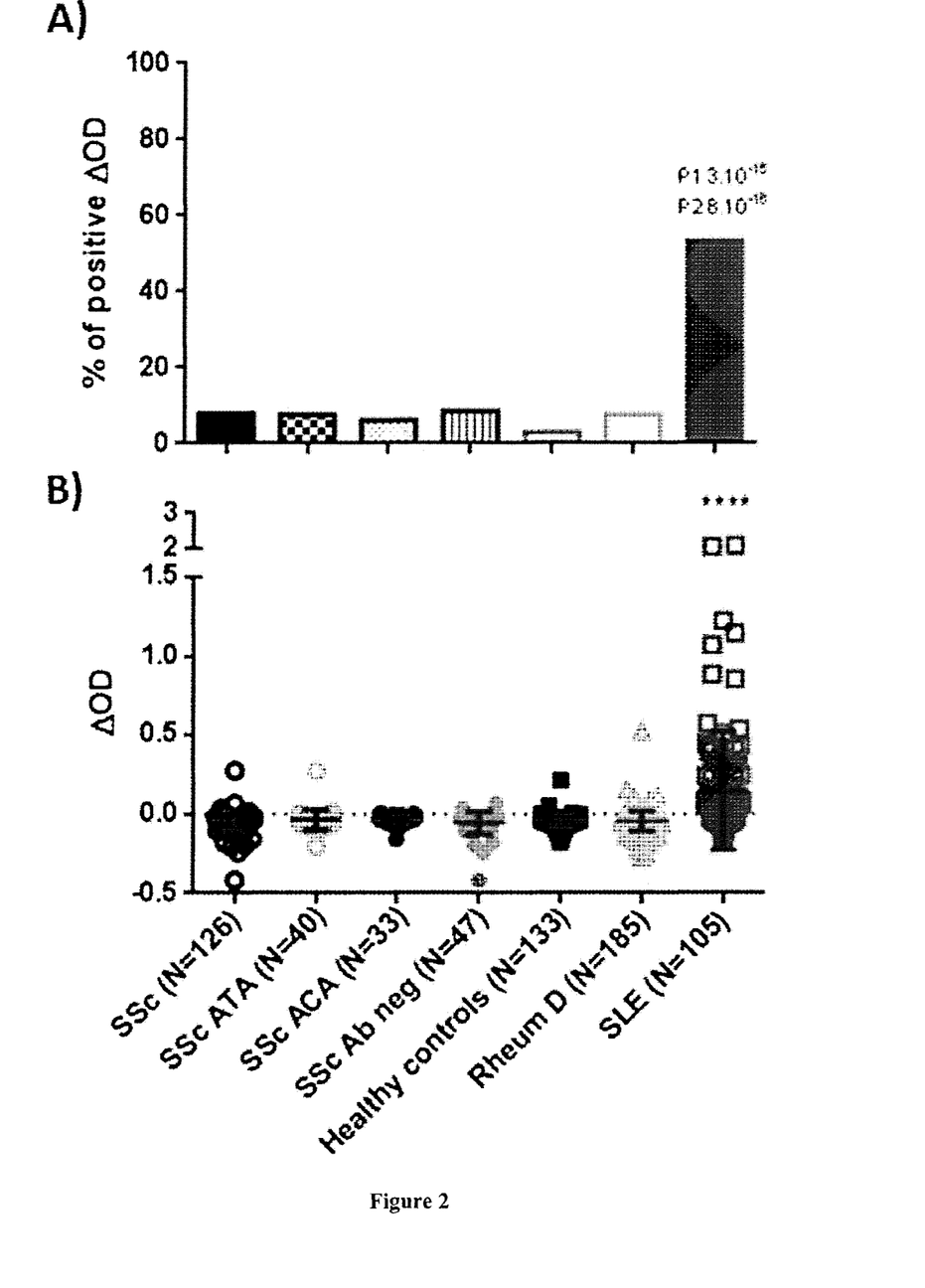
FIG. 2: Autoantibodies to THEX1 (0.1 µg/well) analyzed in subgroups of patients with SSc and other diseases. A) Percentage of positive individuals, B) χOD values.

When tested at a lower concentration of 0.1 μg/well (FIGS. 2A and 2B), only patients with SLE (N=105) remained positive compared to any tested group of patients or all other groups (N=444). Indeed, 53% of patients with SLE recognized the protein with a mean ΔOD of 0.147 compared to only 6% of all other subjects (HC, N=133; Rheum D, N=185; SSc, N=126) with a mean ΔOD for the 444 subjects of −0.042 ($p<10^{-33}$).

THEX1 ΔOD Correlates with Severity of SLE Disease

Figure 3:
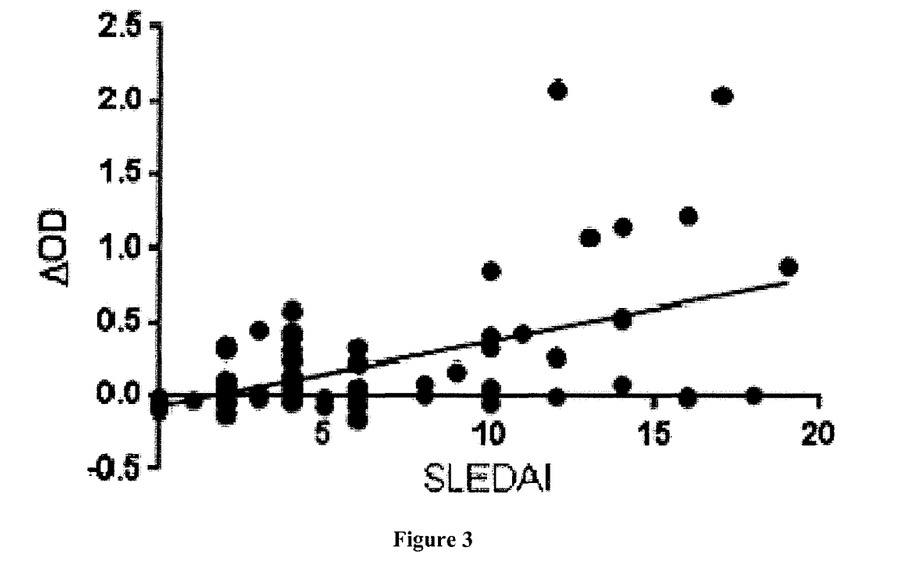
FIG. 3: Correlation between $\chi$OD values and disease severity in patients with SLE (N=84). SLEDAI: Systemic Lupus Erythematosus Disease Activity Index.

We had obtained SLEDAI informations for 84 patients with SLE and could analyze whether THEX1 ΔOD highest values correlated with elevated SLEDAI. We found a significant correlation (Spearman test, FIG. 3) between severity of SLE disease and highest THEX1 autoantibody presence in plasma from patients, indicating THEX1 could be a severity marker.

Additional data: Clinical and serological characteristics of patients with lupus, positive or negative for anti-THEX1 antibodies (at 0.1 μg/well).

There was no significant difference in gender or ethnics between patients with lupus, positive or negative for anti-THEX1 antibodies, but patients who were positive for THEX1 had more often other autoantibodies such as anti-dsDNA, anti-Sm and anti-SSB. Nevertheless it is to note that THEX1 was also useful to identify patients without anti-dsDNA antibodies as it recognized more than a third of them (36%, N=39).

Patients with active disease were more often positive for anti-THEX1 antibodies (p=0.0002). This was confirmed by a significant correlation between SLEDAI and highest THEX1 autoantibody levels in plasma from patients (Spearman's correlation, p<0.0001), indicating that THEX1 could be a marker of activity. Treatments were not different between patients positive or negative for THEX1 autoantibodies. Patients were often under corticoids or hydroxychloroquine and in same proportions in both groups (data not shown).

Conclusion:

Our results revealed that THEX1, tested on a large cohort of SLE patients (N=105) and a large cohort of controls (N=444) is a new marker for SLE diagnosis, with a specificity of 94% and a sensitivity of 53% (at concentrations of 0.1 μg/well). Moreover, THEX1 is a severity marker as THEX1 ΔOD highest values correlated with elevated SLEDAI.

REFERENCES

Throughout this application, various references describe the state of the art to which this invention pertains.

Hochberg M C. Updating the American College of Rheumatology revised criteria for the classification of systemic lupus erythematosus. Arthritis Rheum 1997 September; 40(9):1725.

Petri M, Orbai A M, Alarcon G S, Gordon C, Merrill J T, Fortin P R, et al. Derivation and validation of the Systemic Lupus International Collaborating Clinics classification criteria for systemic lupus erythematosus. Arthritis Rheum 2012 August; 64(8):2677-86.

Sherer Y, Gorstein A, Fritzler M J, Shoenfeld Y. Autoantibody explosion in systemic lupus erythematosus: more than 100 different antibodies found in SLE patients. Seminars in arthritis and rheumatism. [Review]. 2004 October; 34(2):501-37.

Tan E M, Cohen A S, Fries J F, Masi A T, McShane D J, Rothfield N F, et al. The 1982 revised criteria for the classification of systemic lupus erythematosus. Arthritis Rheum 1982 November; 25(11):1271-7.

Vollmann J, Winau R. Informed consent in human experimentation before the Nuremberg code. BMJ. 1996 Dec. 7; 313(7070):1445-9.

---

The invention claimed is:

1. A method of diagnosing and treating lupus in a subject suspected of having lupus, said method comprising the steps of:
   (a) obtaining a biological sample from the subject suspected of having lupus, wherein the biological sample is blood plasma or serum;
   (b) performing an ELISA assay for measuring auto-antibodies to THEX1 protein in the biological sample of (a), wherein the assay comprises:
      (i) immobilizing the THEX1 protein on a solid support comprising wells, at a concentration of 0.1 pg/well, to form a complex with the auto-antibodies to the THEX1 protein present in the biological sample; and
      (ii) detecting the complex, thereby detecting the level of auto-antibodies to the THEX1 protein in the biological sample, wherein the in the THEX1 protein consists of an amino acid sequence of SEQ ID NO: 1;
   (c) comparing the level of auto-antibodies to the THEX1 protein present in the biological sample of (a) with control levels of each of (1) auto-antibodies to the THEX1 protein in blood plasma or serum from healthy subjects and (2) auto-antibodies to the THEX1 protein in blood plasma or serum from subjects with systemic sclerosis (SSc);
   (d) diagnosing the subject as having lupus when the level of auto-antibodies to the THEX1 protein present in the biological sample of (a) is statistically significantly higher than each of the control level of auto-antibodies to the THEX1 protein in blood plasma or serum from healthy subjects and the control level of auto-antibodies to the THEX1 protein in blood plasma or serum from subjects with SSc; and
   (e) treating the diagnosed subject of (d) with corticoids and/or hydroxychloroquine; wherein the control subjects with SSc do not have at least one of anti-topoisomerase autoantibodies and anti-centromere autoantibodies and wherein each of the control level of auto-antibodies to the THEX1 protein of (c) is obtained by performing steps (i) and (ii).

* * * * *

SEQUENCE LISTING

```
<160> NUMBER OF SEQ ID NOS: 1

<210> SEQ ID NO 1
<211> LENGTH: 349
<212> TYPE: PRT
<213> ORGANISM: Homo sapiens

<400> SEQUENCE: 1

Met Glu Asp Pro Gln Ser Lys Glu Pro Ala Gly Glu Ala Val Ala Leu
1               5                   10                  15

Ala Leu Leu Glu Ser Pro Arg Pro Glu Gly Gly Glu Glu Pro Pro Arg
            20                  25                  30

Pro Ser Pro Glu Glu Thr Gln Gln Cys Lys Phe Asp Gly Gln Glu Thr
        35                  40                  45

Lys Gly Ser Lys Phe Ile Thr Ser Ser Ala Ser Asp Phe Ser Asp Pro
    50                  55                  60

Val Tyr Lys Glu Ile Ala Ile Thr Asn Gly Cys Ile Asn Arg Met Ser
65                  70                  75                  80

Lys Glu Glu Leu Arg Ala Lys Leu Ser Glu Phe Lys Leu Glu Thr Arg
                85                  90                  95

Gly Val Lys Asp Val Leu Lys Lys Arg Leu Lys Asn Tyr Tyr Lys Lys
            100                 105                 110
```

```
Gln Lys Leu Met Leu Lys Glu Ser Asn Phe Ala Asp Ser Tyr Tyr Asp
        115                 120                 125

Tyr Ile Cys Ile Ile Asp Phe Glu Ala Thr Cys Glu Glu Gly Asn Pro
        130                 135                 140

Pro Glu Phe Val His Glu Ile Ile Glu Phe Pro Val Val Leu Leu Asn
145                 150                 155                 160

Thr His Thr Leu Glu Ile Glu Asp Thr Phe Gln Gln Tyr Val Arg Pro
                165                 170                 175

Glu Ile Asn Thr Gln Leu Ser Asp Phe Cys Ile Ser Leu Thr Gly Ile
            180                 185                 190

Thr Gln Asp Gln Val Asp Arg Ala Asp Thr Phe Pro Gln Val Leu Lys
        195                 200                 205

Lys Val Ile Asp Trp Met Lys Leu Lys Glu Leu Gly Thr Lys Tyr Lys
        210                 215                 220

Tyr Ser Leu Leu Thr Asp Gly Ser Trp Asp Met Ser Lys Phe Leu Asn
225                 230                 235                 240

Ile Gln Cys Gln Leu Ser Arg Leu Lys Tyr Pro Pro Phe Ala Lys Lys
            245                 250                 255

Trp Ile Asn Ile Arg Lys Ser Tyr Gly Asn Phe Tyr Lys Val Pro Arg
            260                 265                 270

Ser Gln Thr Lys Leu Thr Ile Met Leu Glu Lys Leu Gly Met Asp Tyr
        275                 280                 285

Asp Gly Arg Pro His Cys Gly Leu Asp Asp Ser Lys Asn Ile Ala Arg
        290                 295                 300

Ile Ala Val Arg Met Leu Gln Asp Gly Cys Glu Leu Arg Ile Asn Glu
305                 310                 315                 320

Lys Met His Ala Gly Gln Leu Met Ser Val Ser Ser Ser Leu Pro Ile
                325                 330                 335

Glu Gly Thr Pro Pro Gln Met Pro His Phe Arg Lys
            340                 345
```